(12) United States Patent
Lin

(10) Patent No.: US 10,537,687 B2
(45) Date of Patent: Jan. 21, 2020

(54) NEEDLE PROTECTION DEVICE AND SAFETY NEEDLE ASSEMBLY

(75) Inventor: Zuoqian Lin, Wenling (CN)

(73) Assignee: SOL-MILLENNIUM MEDICAL HK LIMITED, Hong Kong (CN)

(*) Notice: Subject to any disclaimer, the term of this patent is extended or adjusted under 35 U.S.C. 154(b) by 1019 days.

(21) Appl. No.: 14/342,222

(22) PCT Filed: Aug. 28, 2012

(86) PCT No.: PCT/CN2012/080666
§ 371 (c)(1),
(2), (4) Date: Feb. 28, 2014

(87) PCT Pub. No.: WO2013/029529
PCT Pub. Date: Mar. 7, 2013

(65) Prior Publication Data
US 2014/0221872 A1    Aug. 7, 2014

(30) Foreign Application Priority Data
Sep. 1, 2011 (CN) .......................... 2011 1 0270127

(51) Int. Cl.
*A61M 5/32* (2006.01)
*A61B 5/15* (2006.01)

(52) U.S. Cl.
CPC ..... *A61M 5/3216* (2013.01); *A61B 5/150664* (2013.01)

(58) Field of Classification Search
CPC ........ A61M 2005/3217; A61M 5/1626; A61M 5/3202; A61M 5/321; A61M 5/3216;
(Continued)

(56) References Cited

U.S. PATENT DOCUMENTS

| 3,669,111 A | 6/1972 | Dubner |
| 4,346,708 A | 8/1982 | Leveen et al. |

(Continued)

FOREIGN PATENT DOCUMENTS

| CA | 2214447 | 3/1998 |
| CN | 1152882 A | 6/1997 |

(Continued)

OTHER PUBLICATIONS

Patent Examination Report from counterpart Australian Application No. 2012303935, dated Apr. 4, 2016, 3 pp.

(Continued)

*Primary Examiner* — Bhisma Mehta
*Assistant Examiner* — Laura C Schell
(74) *Attorney, Agent, or Firm* — Shumaker & Sieffert, P.A.

(57) ABSTRACT

A needle protection device and a safety needle assembly are described. The needle protection device comprises a connecting portion and a protection arm rotatable relative to the connecting portion. A pair of holding members are respectively formed on a proximal end portion of the protection arm and the connecting portion and configured to engage with each other in an unretreatable manner. A pair of positioning arms are respectively formed on the proximal end portion of the protection arm and the connecting portion and formed with at least one pair of complementary snap-fitting features. The paired snap-fitting features are configured to engage each other in a separable manner. The needle protection device and the safety needle assembly not only reliably prevents medical instruments from incurring accidental needle-sticks after use and ensures such medical instruments disposable, but also exhibits a simple structure and low costs.

9 Claims, 17 Drawing Sheets

(58) Field of Classification Search
CPC ........ A61M 5/3219; A61M 5/158–2005/1588;
A61M 25/06–25/0637; A61M 5/162;
A61M 5/32; A61B 5/150664–5/150687;
A61B 5/150633–5/150656; A61B
5/150534; A61B 5/150557; A61B
5/150564; A61B 5/15058–5/150625
See application file for complete search history.

(56) References Cited

U.S. PATENT DOCUMENTS

| | | | |
|---|---|---|---|
| 5,279,420 A | 1/1994 | Rodgers | |
| 5,312,369 A | 5/1994 | Arcusin et al. | |
| 5,352,200 A | 10/1994 | Hammett et al. | |
| 5,599,313 A * | 2/1997 | Gyure | A61M 5/3216 604/111 |
| 5,649,622 A | 7/1997 | Hollister | |
| 5,662,617 A * | 9/1997 | Odell | A61M 5/3216 128/919 |
| 5,733,265 A | 3/1998 | Bachman et al. | |
| 6,120,482 A | 9/2000 | Szabo | |
| 6,391,008 B1 * | 5/2002 | Tsai | A61M 5/322 604/110 |
| 7,798,993 B2 | 9/2010 | Lim | |
| 8,251,961 B2 | 8/2012 | Hauri et al. | |
| 8,622,960 B2 | 1/2014 | Madin et al. | |
| 8,641,680 B2 | 2/2014 | Simas, Jr. | |
| 9,333,301 B2 | 5/2016 | Alheidt et al. | |
| 9,566,392 B2 | 2/2017 | Jiang et al. | |
| 9,662,456 B2 | 5/2017 | Woehr | |
| 2002/0193744 A1 | 12/2002 | Alesi et al. | |
| 2003/0181874 A1 | 9/2003 | Bressler et al. | |
| 2005/0080381 A1 | 4/2005 | Hsieh et al. | |
| 2005/0107747 A1 | 5/2005 | Shih | |
| 2006/0178625 A1 | 8/2006 | Lim et al. | |
| 2007/0073223 A1 | 3/2007 | Huang | |
| 2007/0270753 A1 | 11/2007 | Kulli | |
| 2008/0177234 A1 * | 7/2008 | Keaton | A61M 25/02 604/177 |
| 2008/0208138 A1 | 8/2008 | Lim et al. | |
| 2009/0018510 A1 | 1/2009 | Madin et al. | |
| 2010/0049141 A1 | 2/2010 | Gardner | |

FOREIGN PATENT DOCUMENTS

| | | |
|---|---|---|
| CN | 1701822 A | 11/2005 |
| CN | 1961982 A | 5/2007 |
| CN | 101098725 A | 1/2008 |
| CN | 101287514 A | 10/2008 |
| CN | 101687083 A | 3/2010 |
| CN | 101743027 A | 6/2010 |
| CN | 101790396 A | 7/2010 |
| CN | 101862490 A | 10/2010 |
| CN | 202113434 U | 1/2012 |
| CN | 202270231 U | 6/2012 |
| CN | 202569095 U | 12/2012 |
| EP | 0832660 A2 | 4/1998 |
| EP | 2554204 A1 | 2/2013 |
| JP | 7507985 A | 9/1995 |
| JP | 10113392 A | 5/1998 |
| JP | 2006501944 A | 1/2006 |
| JP | 2007505722 A | 3/2007 |
| JP | 2008526361 A | 7/2008 |
| JP | 2010533020 A | 10/2010 |
| RU | 2065757 C1 | 8/1996 |
| WO | 9323312 A1 | 11/1993 |
| WO | 9530444 A1 | 11/1995 |
| WO | 9906086 A1 | 2/1999 |
| WO | 2004033006 A2 | 4/2004 |
| WO | 2005030290 A2 | 4/2005 |
| WO | 2007019170 A1 | 2/2007 |
| WO | 2010139793 A1 | 12/2010 |
| WO | 2011160364 A | 12/2011 |
| WO | 2013153121 A2 | 10/2013 |

OTHER PUBLICATIONS

Examination Report from counterpart European Application No. 12826696.2, dated Aug. 31, 2015, 5 pp.
Office Action, and a partial translation thereof, from counterpart Japanese Application No. 2014-527482, dated Nov. 8, 2016, 4 pp.
Office Action, and a translation thereof, from counterpart Russian Application No. 2014112243/14, dated Dec. 29, 2016, 6 pp.
Extended Search Report from counterpart European Application No. 12826696.2, dated Oct. 20, 2014, 7 pp.
Notification of Transmittal of the International Search Report and the Written Opinion of the International Searching Authority, or the Declaration dated Nov. 22, 2012 in corresponding PCT Application No. PCT/CN2012/080666, 14 pgs.
Examination from counterpart Mexican Patent Application No. MX/a/2014/002419, 3 pp.
Non-final Rejection and Translation thereof, dated Jul. 27, 2017 in counterpart Russian Application 2014112242, 7 pps.
Office Action and Search Report, and partial translation thereof, from counterpart Chilean Application No. PCT/2014-000507, dated Jul. 6, 2017, 13 pp.
Office Action, and translation thereof, from counterpart Russian Application No. PCT/CN2012/080666, dated Feb. 7, 2017, 6 pp.
Office Action and translation thereof, from counterpart Chilean Application No. PCT/CN2012/080666, dated Feb. 8, 2018, 14 pp.
Office Action from counterpart Canadian Application No. 2,847,183, dated May 17, 2018, 8 pp.
Office Action from counterpart Malaysian Application No. PI 2014700484, dated Apr. 13, 2018, 3 pp..

* cited by examiner

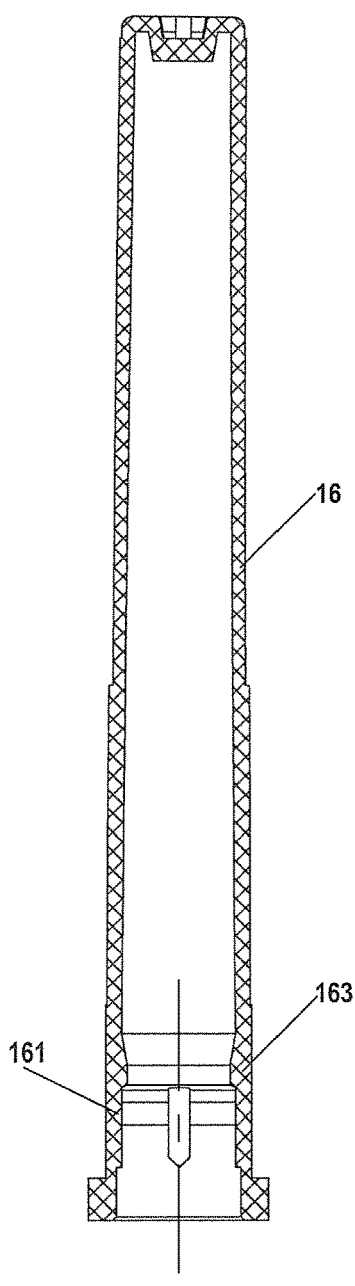
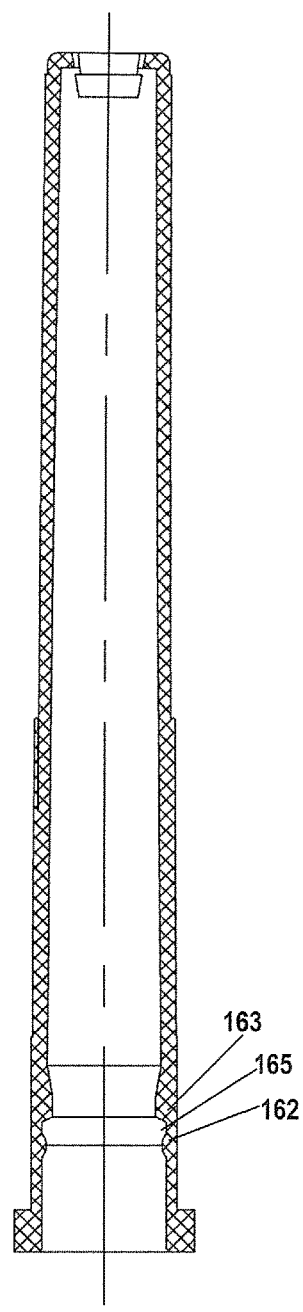
Fig. 13
Fig. 15
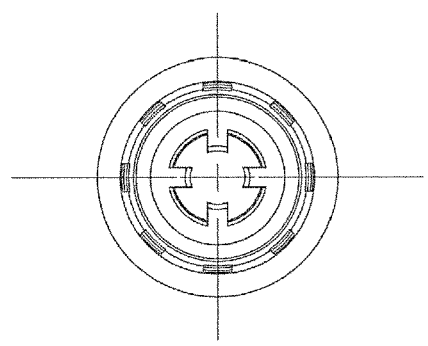
Fig. 14

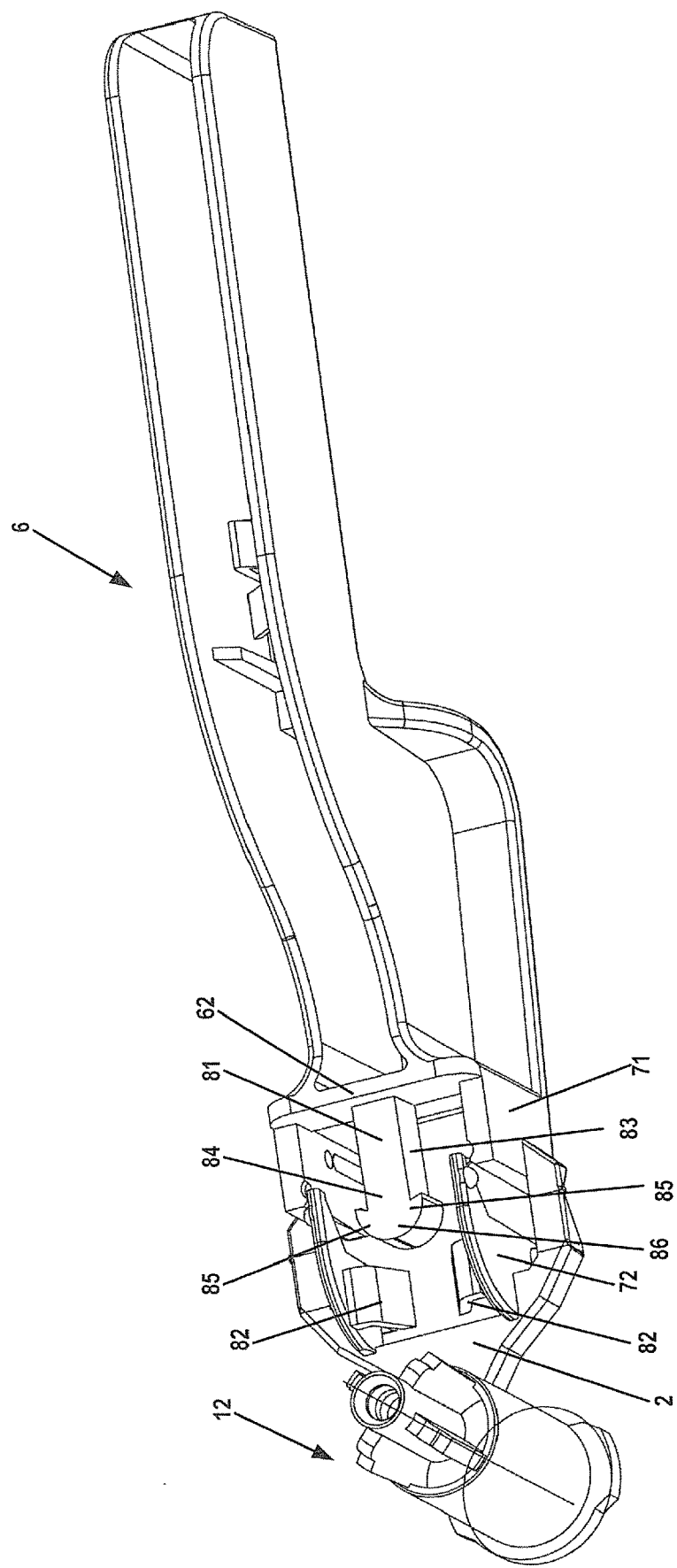

NEEDLE PROTECTION DEVICE AND SAFETY NEEDLE ASSEMBLY

CROSS REFERENCE TO RELATED APPLICATIONS

This application is a national stage entry under 35 U.S.C. § 371 of PCT Application No. PCT/CN2012/080666, filed Aug. 28, 2012, which claims the benefit of Chinese Application No. 201110270127.1, filed Sep. 1, 2011. The entire contents of PCT Application No. PCT/CN2012/080666 and Chinese Application No. 201110270127.1 are incorporated herein by reference.

TECHNICAL FIELD

The present invention relates to a needle protection device, and particularly a needle protection device which can prevent a needle used in medical instruments such as a syringe and a blood collector from incurring accidental needle-sticks after use. The present invention further relates to a safety needle assembly comprising such needle protection device.

BACKGROUND

In medical practice, medical instruments with a pointed needle are used very extensively, such as syringes and blood collectors. These medical instruments are used and treated by not only professionals in medical institutions but also non-professionals at home, e.g., a diabetes patient injects insulin on his own.

Such a medical instrument as a syringe may leave its needle to be exposed outside after use and likely stick relevant persons, which causes considerable difficulty to collection and treatment thereof. Such needle-stick might cause infection of bacteria.

In order to prevent occurrence of accidental needle-sticks, syringes with needles capable of being retracted after use have been proposed. However, such syringes are structurally complicated and costly.

SUMMARY

Accordingly, in order to prevent medical instruments such as a syringe and a blood collector with a needle from incurring accidental needle-sticks after use with a simple structure and low costs, an aspect of the present invention provides a needle protection device comprising a connecting portion configured to be engaged with a needle hub of a needle, a protection arm configured to receive a needle tube of the needle therein, and a hinge member. The hinge member is connected between the connecting portion and the protection arm so that the protection arm is rotatable relative to the connecting portion. The needle protection device further comprises a pair of holding members formed on a proximal end portion of the protection arm and the connecting portion respectively. When the protection arm rotates to a full protection position in which it is most approximate to the needle tube of the needle relative to the connecting portion, the pair of holding members are configured to be engaged in an unretreatable manner. Preferably, the needle protection device further comprises a pair of positioning arms formed on the proximal end portion of the protection arm and the connecting portion respectively. At least one pair of complementary snap-fitting features are formed on the pair of positioning arms. The at least one pair of snap-fitting features are configured to engage each other in a separable manner when the protection arm rotates to at least one middle position relative to the connecting portion, wherein the middle position is remote from the needle tube of the needle relative to the full protection position so that at the middle position, the pair of holding members are in non-engaged position, i.e., the pair of holding members are configured not to engage each other in the unretreatable manner.

Another aspect of the present invention provides a safety needle assembly comprising a needle and the above-mentioned needle protection device. The needle comprises a needle tube and a needle hub. The needle hub may comprise a cone and a needle receiving portion located at a central position of a top end of the cone. The cone has a conical socket or conical fitting (female fitting) for mating with a nozzle or conical fitting (male fitting) of a syringe barrel to fix the needle hub on the syringe barrel. In an interior of the needle receiving portion is formed an inner bore for receiving the needle tube. The needle hub further comprises a plurality of ribs which are connected between an upper edge of the cone and a circumferential surface of the needle receiving portion to suspend the needle receiving portion. A front end of the rib expands radially outwardly to form a projection.

In the present invention, the pair of positioning arms comprise a first positioning arm and a second positioning arm which are located on the same side of the first and second holding members and configured to be engaged with each other.

Preferably, the needle protection device may comprise two pairs of positioning arms symmetrically located on both sides of the pair of holding members. The pair of holding members may comprise: a first holding member comprising a first column-like portion and an anchor formed on the first column-like portion; and a second holding member comprising one or more paws formed on an edge of a through hole. The one or more paws extend towards a center of the through hole. Distal ends of the paws, or the distal ends of the paws and the edge of the through hole which has a maximum radial dimension smaller than a maximum radial dimension of a base of the anchor. Wherein the one or more paws are configured such that the distal ends of the paws enable a front end of the anchor to pass through the through hole and catch the base of the anchor in an unretreatable manner when the protection arm rotates to the full protection position.

The first holding member may be formed on the proximal end portion of the protection arm. The second holding member may be formed on the connecting portion. The through hole may be formed on the connecting portion. The paws are formed on the edge of the through hole, and extend towards a center of the through hole and are inclined towards a side opposite the side in which the first holding member lies, so that when the protection arm rotates to the full protection position, the front end of the anchor can pass through the through hole and beyond the paws, and the base thereof is caught by the paws in an unretreatable manner.

Or, the first holding member may be formed on the connecting portion, and the second holding member may be formed on the proximal end portion of the protection arm. The through hole may be formed on the proximal end portion of the protection arm. The paws are formed on the edge of the through hole, and extend towards a center of the through hole and are inclined towards a side opposite the side in which the first holding member lies, so that when the protection arm rotates to the full protection position, the front end of the anchor can pass through the through hole and beyond the paws, and the base thereof is caught by the paws in an unretreatable manner.

The first holding member may further comprise a second column-like portion between the anchor and the first column-like portion which has a maximum radial dimension smaller than that of the first column-like portion. The anchor is an extending tip portion, and a maximum radial dimension of the base of the anchor is larger than that of the second column-like portion.

As another embodiment, the pair of holding members may comprise a first holding member formed with a hook-like portion at a free end thereof and a second holding member in the form of a plate-like hook, wherein the hook-like portion of the first holding member and the second holding member are configured to engage each other in an unretreatable manner when the protection arm rotates to the full protection device.

Preferably, the first holding member may be formed on the proximal end portion of the protection arm, and the second holding member may be formed on the connecting portion.

In another embodiment, the first holding member may be plate-shaped and formed on the proximal end portion of the protection arm, and the hook-like portion is formed on each of two opposite thickness surfaces of the free end thereof. The needle protection device may comprise two pairs of positioning arms symmetrically located on both sides of the first holding member. The positioning arm of each pair of positioning arms formed on the connecting portion is formed with a second holding member. The two hook-like portions of the first holding member and the two second holding members are configured to engage each other in an unretreatable manner when the protection arm rotates to the full protection device.

Preferably, a widthwise dimension may gradually increase from the free end of the first holding member to the hook-like portion.

Preferably, an additional hook-like portion is formed on one widthwise surface of the free end of the first holding member, an additional second holding member is formed on the connecting portion, so that the three hook-like portions of the first holding member are respectively engaged with the three second holding members in an unretreatable manner when the protection arm rotates to the full protection position.

According to the present invention, each pair of positioning arms may comprise a first positioning arm and a second positioning arm. A first protrusion may be formed on an end portion of the second positioning arm extending towards the first positioning arm, a first concave may be at least formed on a path on the first positioning arm formed by movement relative to the first protrusion. The first protrusion is configured to engage with the first concave in a separable manner to position the protection arm at a first middle position (first in-use position). Therefore, the first protrusion and the first concave constitute a first pair of snap-fitting features.

A second concave may be additionally formed on the path on the first positioning arm formed by movement relative to the first protrusion. The first protrusion is configured to engage with the second concave in a separable manner to position the protection arm at a second middle position (packaged position). Therefore, the first protrusion and the second concave constitute a second pair of snap-fitting features.

The second positioning arm may comprise an upper second positioning arm and a lower second positioning arm. The first protrusion may be formed on an end portion of the upper second positioning arm extending towards the first positioning arm. The first protrusion is configured to engage with the first concave and the second concave in turn when the protection arm rotates in the direction of the full protection position relative to the connecting portion.

A second protrusion may be formed at a lower edge of the lower second positioning arm. At least one third concave is formed on a path on the first positioning arm formed by movement relative to the second protrusion. The second protrusion is configured to engage with the third concave in a separable manner to position the protection arm at a third middle position (second in-use position). Therefore, the second protrusion and the third concave constitute a third pair of snap-fitting features.

A fourth concave may be additionally formed on the path on the first positioning arm formed by movement relative to the first protrusion. The first protrusion is configured to engage with the fourth concave in a separable manner to position the protection arm at a fourth middle position (a temporary protection position) adjacent to the full protection position. When the protection arm rotates to the temporary protection position, the needle tube is located in the opening of the protection arm, and the first and the second holding members are in non-engaged position in which the holding members are configured not to engage the second holding members in an unretreatable manner.

The safety needle assembly according to the present invention may further comprise a needle cap for receiving and covering said needle tube which has a lower end of the needle cap configured to be disposed around the needle receiving portion. The needle cap may comprise two flanges formed on an inner surface of the lower end of the needle cap, so that an annular groove is formed between the two flanges. The projections of the ribs are configured to be snap-fitted in the groove in a separable manner to prevent the needle cap from moving axially relative to the needle.

The needle protection device and the safety needle assembly according to the present invention can not only reliably prevent medical instruments such as syringes from incurring accidental needle-sticks after use and ensure such medical instruments disposable, but also exhibit a simple structure and low costs. Additionally, according to the present invention, during transport and use of the safety needle assembly, the needle protection device can be stably positioned at various desired positions.

BRIEF DESCRIPTION OF THE DRAWINGS

FIG. 13 is a cross-sectional view of the needle cap of FIG. 1.

FIG. 14 is a bottom view of the needle cap of FIG. 13.

FIG. 15 is a cross-sectional view of the needle cap analogous to FIG. 13, with the needle cap be rotated by an angle.

FIG. 16 is a perspective view of a needle protection device according to another embodiment of the present invention.

DETAILED DESCRIPTION

Preferred embodiments of a needle protection device of the invention and a safety needle assembly including this needle protection device will be described in detail with reference to the accompanying drawings.

Figure 1:
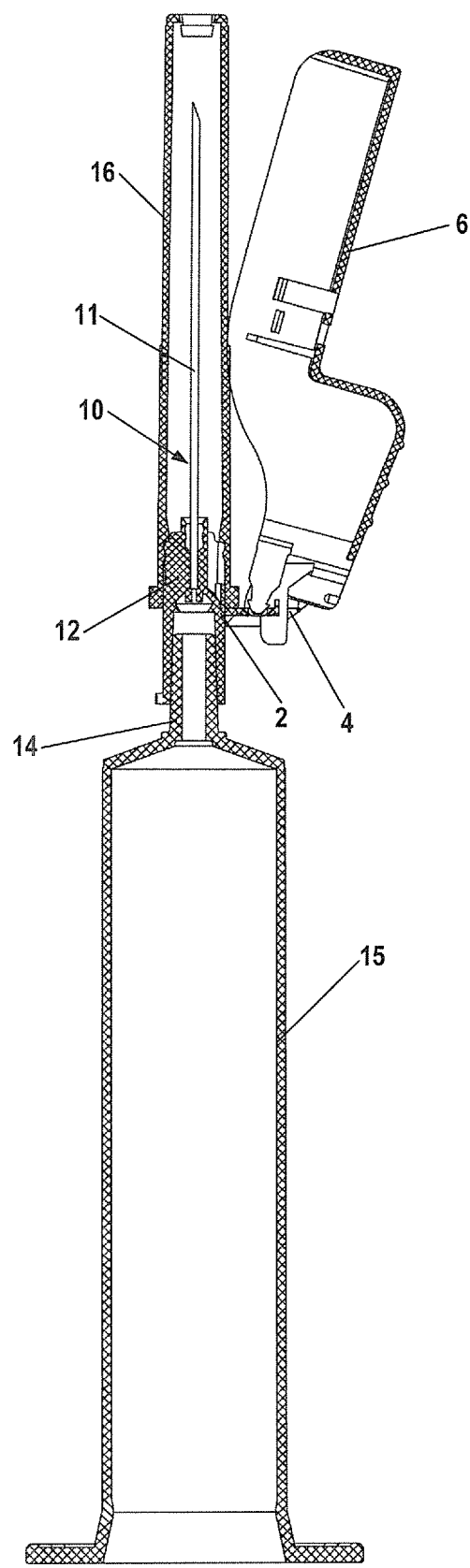
FIG. 1 is a cross-sectional view of a safety needle assembly according to an embodiment of the present invention, with a protection arm being in a packaged position.

FIG. 1 shows a safety needle assembly according to the present invention in a packaged state before use. The safety needle assembly comprises a needle 10, a needle protection device and a needle cap 16.

The needle 10 comprises a needle hub 12 and a needle tube 11 mounted on the needle hub 12. In some applications such as for injectors or syringes, the needle 10 is also called "injection needle", and the needle tube 11 is also called a "needle". The present invention is not directed to improvement to the needle 10 itself. Therefore, various needles needing protection after use known in the art all can be used to construct the safety needle assembly of the present invention. The safety needle assembly of the present invention may be, but not limited to one of a safety blood collection, a safety syringe assembly, a safety assembly for insulin, a safety single or dual flap butterfly needle (or called scalp needle) assembly.

Also referring to FIGS. 6, 8, 9 and 11, in an embodiment of the present invention, the needle hub 12 comprises cone 121. The cone 121 has a conical fitting (female fitting) for mating with a conical fitting (male fitting) 14 of a syringe barrel 15 to fix the needle hub 12 on the syringe barrel 15. At a central position of a top end of cone 121, the needle hub 12 further comprises a needle receiving portion 123 suspended by a plurality of ribs 122. In an interior of the needle receiving portion 123 is formed an inner hole for receiving the needle 11. The plurality of ribs 122 may be symmetrically arranged and connected between an upper edge of cone 121 and an outer circumferential surface of the needle receiving portion 123. Although four ribs are shown in the figures, apparently the present invention is not limited thereto. A front end (namely, an end facing towards an inward depth of the needle cap 16) of the rib 122 expands radially outwardly to form a projection 124.

Referring to FIGS. 13-15, the needle cap 16 is a hollow member configured to receive and cover the needle tube 11. A lower end of the needle cap 16 (namely, an end of the needle cap having an opening) is disposed around the needle receiving portion 123, and two flanges 163 and 162 are formed on an inner surface of the needle cap, wherein a first flange 162 is closer to the lower end. A second flange 163 further away from the lower end may be larger than the first flange to abut against the front end of the rib 122. An annular groove 165 is formed between the first flange 162 and the second flange 163. The projection 124 of the rib 122 is configured to pass over the first flange 162 and be snap-fitted in the groove 165, thereby preventing an axial movement of the needle cap 16 relative to the needle hub 12, and preventing the needle cap 16 from accidentally separating from the needle hub 12 in the axial direction during transport. In use, a slight force can be applied so that the projection 124 separates from the groove 165 and passes over the first flange 162, thereby removing the needle cap 16.

In the present invention, a separable snap-fitting means that two snap-fitting features, such as the above-described flange and groove and hereunder-described protrusion and recess, are snap-fitted together and can be separated from each other by applying a suitable force.

Those skilled in the art should appreciate that the safety needle assembly of the present invention is not limited to inclusion of the above-described needle cap and needle hub, but can employ various needle hubs and needle caps known in the art. A main object of the present invention does not lie in the needle cap and the needle hub.

Figure 6:
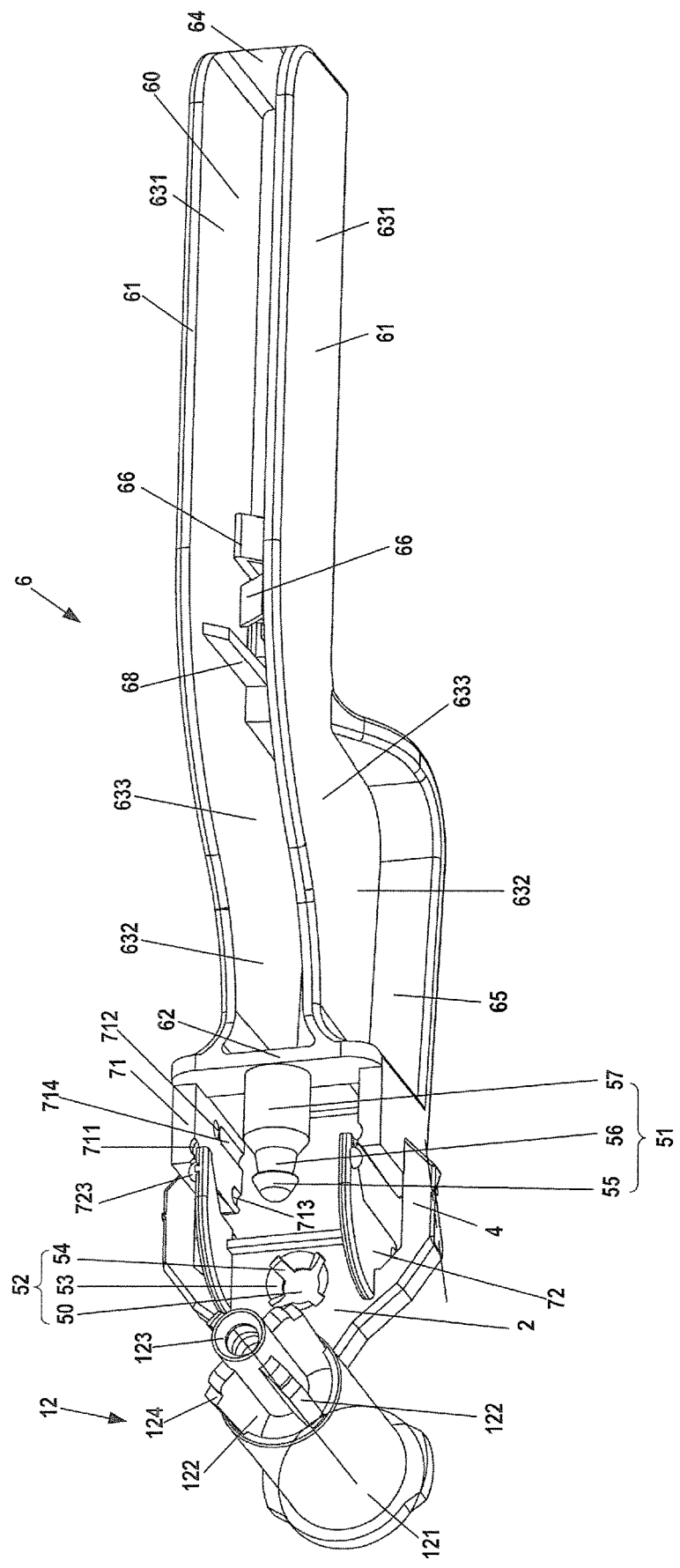
FIG. 6 is a perspective view of a needle hub and a needle protection device of FIG. 1 as viewed obliquely from the above.

Referring to FIGS. 6-12, particularly FIG. 6, the needle protection device comprises a connecting portion 2 configured to be engaged with the needle hub 12 and a protection arm 6 configured to be rotatably engaged with the connecting portion 2 via a hinge member 4.

The connecting portion 2 may be fixedly engaged with the needle hub 12 in any one of various known methods. For example, the connecting portion 2 may be integrally formed with the cone 121 of the needle hub 12 by injection molding, extends outwardly and widens from the side of the cone 121 to form other structures on the connecting portion.

Alternatively, the connecting portion 2 is fixedly disposed around the outer circumferential surface of the needle hub 2 via an annular member (not shown). This embodiment is advantageous in that the needle protection device of the present invention can be directly applied to the conventional safety needle assemblies.

The connecting portion 2 may be engaged at any desired position of the needle hub 12. For example, the connecting portion may be engaged at a position of the cone 121 adjacent to the needle receiving portion (see FIG. 8), whereby the length of the protection arm can be reduced.

Figure 7:
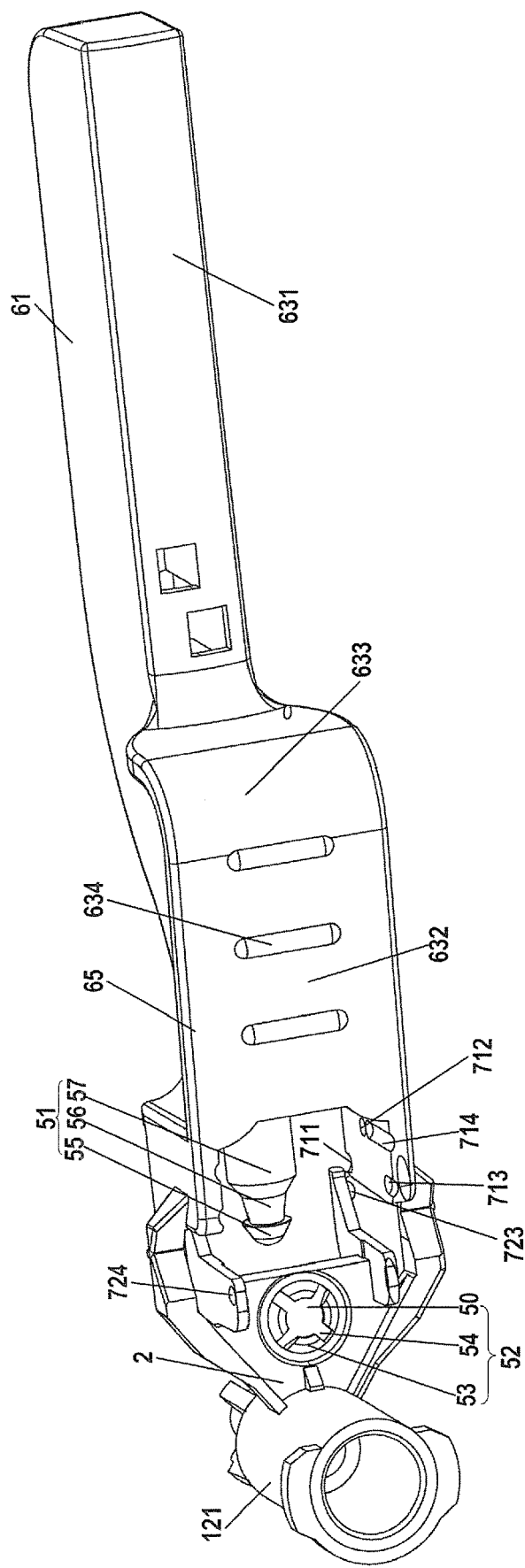
FIG. 7 is a perspective view of a needle hub and a needle protection device of FIG. 1 as viewed from below.

The hinge member 4 rotatably connecting the connecting portion 2 to the protection arm 6 may be one of various hinges known in the art, preferably a hinge formed by injection molding, such as a weakened structure. In a preferred embodiment as shown in the figures, the hinge member 4 is integral with the connecting portion 2, or the hinge member 4 is part of the connecting portion 2. Referring to FIGS. 6 and 7, the connecting portion 2 is wholly substantially fork-shaped or "Y"-shaped. Two prongs of the fork may be formed into the hinge member 4 by forming a weakened portion on each prong of the fork. Alternatively, the hinge member 4 may be integral with the protection arm 6. Again alternatively, the hinge member 4 may be an individual part, and its two ends are respectively fixedly engaged with the connecting portion 2 and the protection arm 6 in the subsequent manufacturing procedure.

Figure 3:
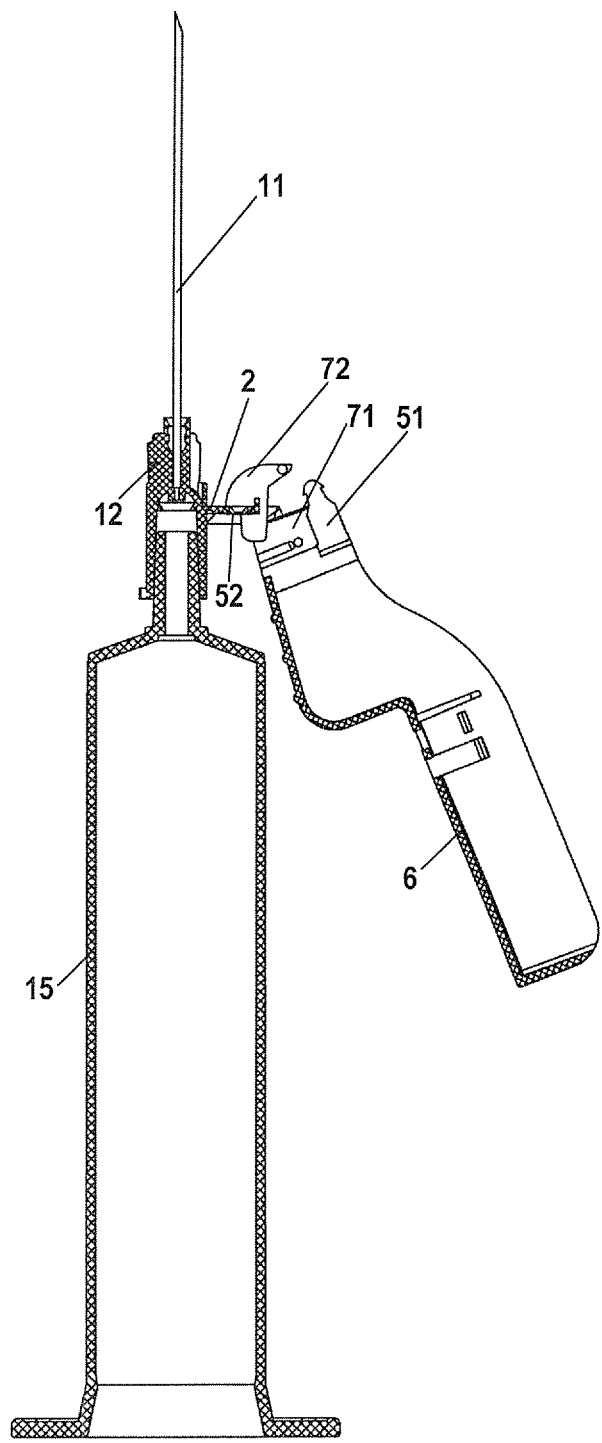
FIG. 3 is a cross-sectional view of the safety needle assembly of FIG. 1, with the protection arm being in a second in-use position.
Figure 4:
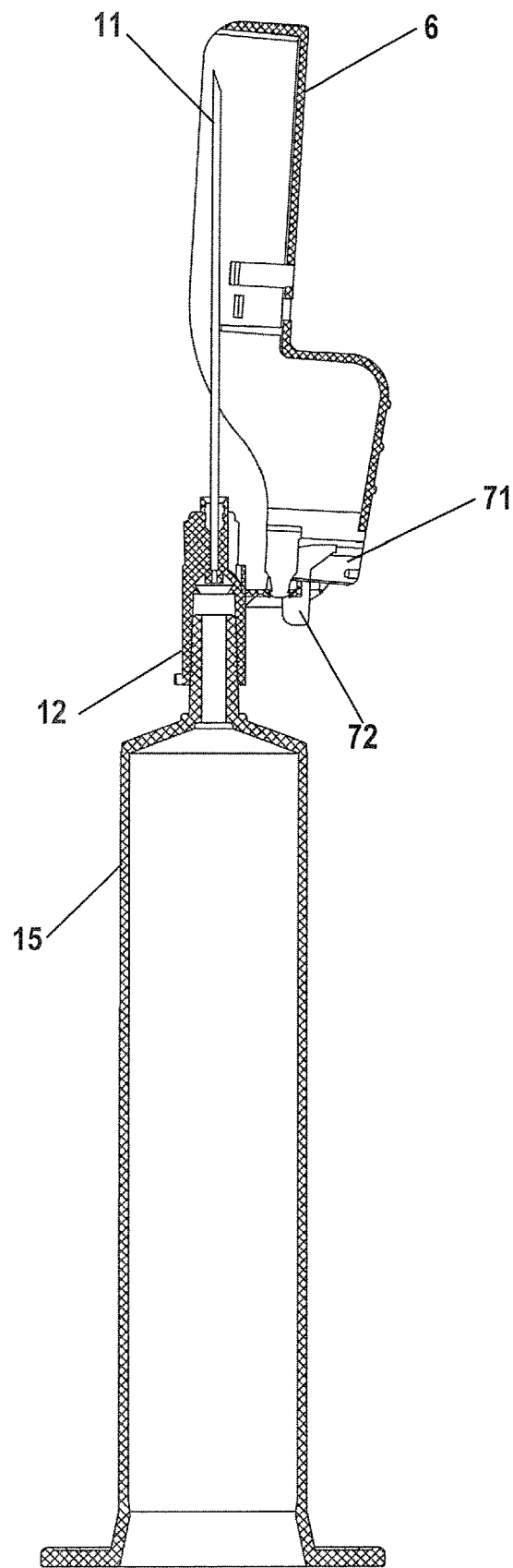
FIG. 4 is a cross-sectional view of the safety needle assembly of FIG. 1, with the protection arm being in a temporary protection position.
Figure 5:
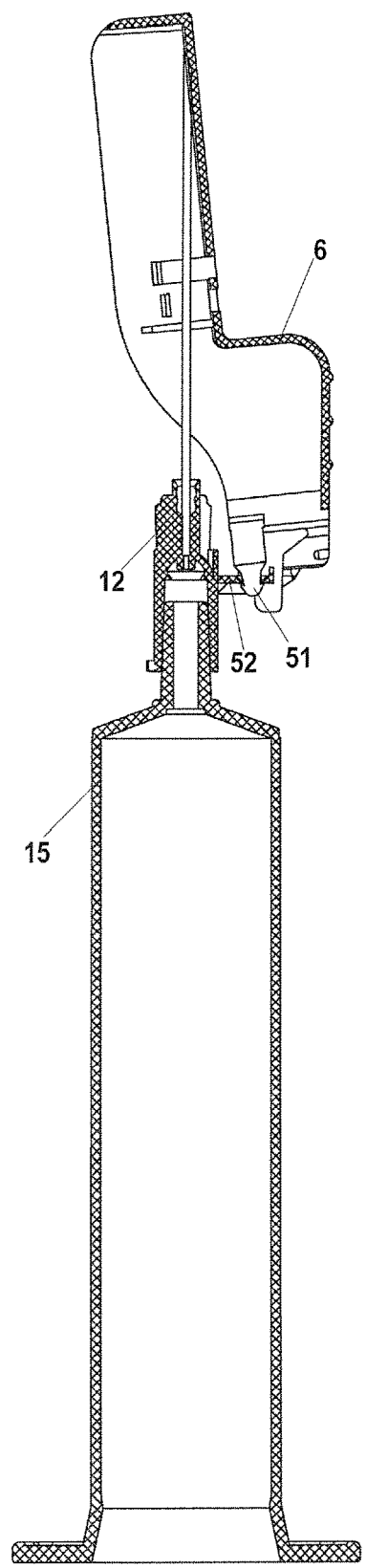
FIG. 5 is a cross-sectional view of the safety needle assembly of FIG. 1, with the protection arm being in a full protection position.

The protection arm 6 is configured to be rotated relative to the needle hub 12 via the hinge member 4, and retained at one of various desired positions, for instance, a full protection position closest to the needle tube 11 as shown in FIG. 5, and a first middle portion to a fourth middle position remote from the needle tube 11 as shown in FIGS. 1-4.

What is shown in FIG. 5 is an after-use state of the safety needle assembly, whereupon the protection arm 6 is rotated to the position closest to the needle tube 11, namely, the full protection position, in which the needle tube 11 is fully received therein.

Figure 2:
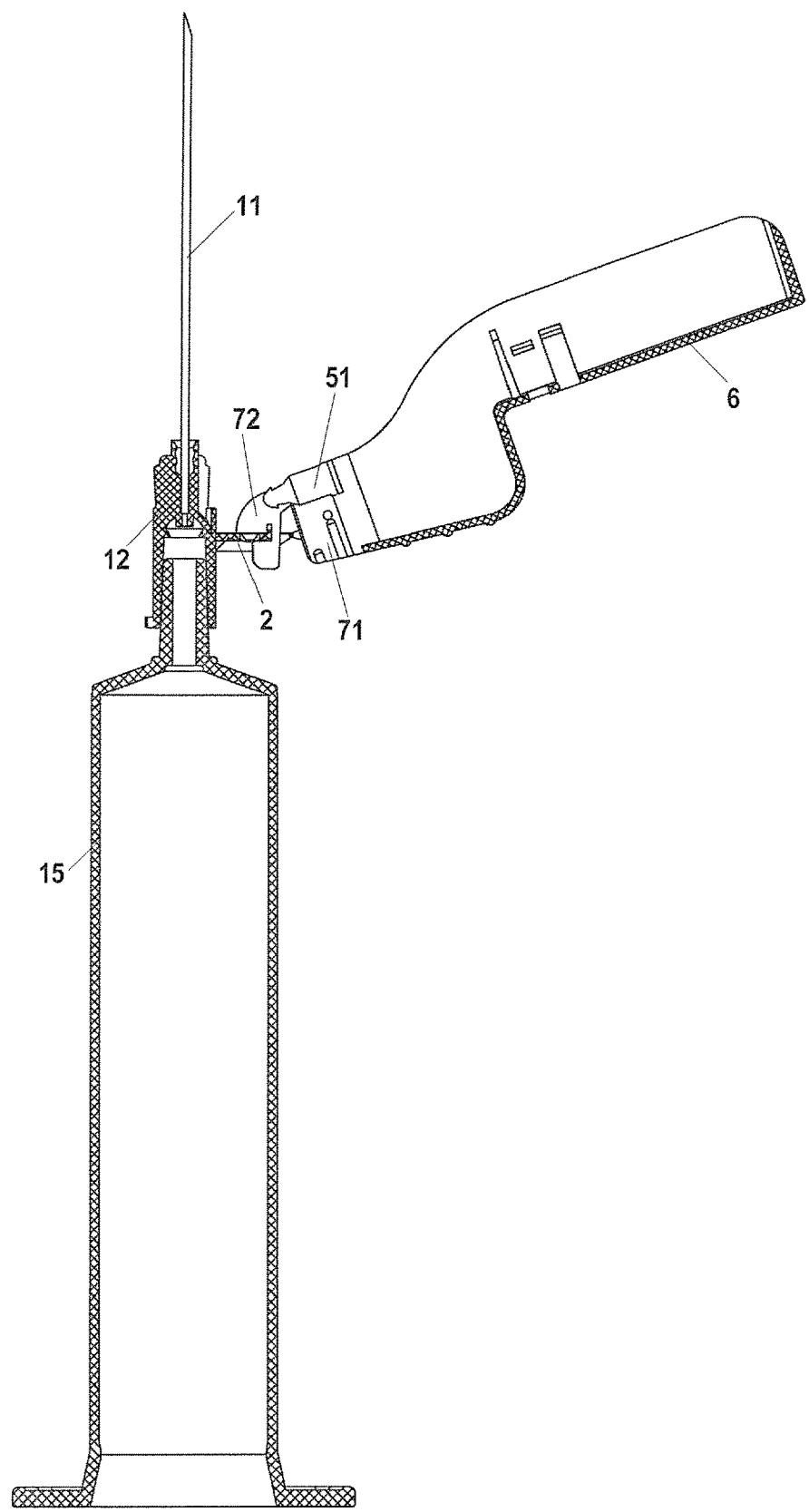
FIG. 2 is a cross-sectional view of the safety needle assembly of FIG. 1, with the protection arm being in a first in-use position.

FIG. 2 and FIG. 3 show two in-use states of the safety needle assembly, whereupon the needle cap 16 is removed, the protection arm 6 is rotated to a position remote from the needle tube 11 (or adjacent to the needle syringe 15), namely, the in-use position. According to different applications, the protection arm 6 may have various different in-use positions, e.g., at an in-use position shown in FIG. 2 (a first in-use position or the first middle position), the protection arm 6 may be at such an angle as 20° relative to a horizontal direction; at an in-use position shown in FIG. 3 (a second in-use position or a third middle position), the protection arm 6 may be opened to the extremity, i.e., at an extreme position away from the needle tube 11 (or towards the syringe barrel 15).

FIG. 1 shows a safety needle assembly in a packaged state before use in which a needle cap 16 covers the needle tube 11, and the protection arm 6 is located at a position adjacent to the needle tube 11 (or the needle cap 16), namely, a packaged position (a second middle position). It may be appreciated that the more the protection arm 6 is adjacent to the needle tube 11 (or needle cap 16), the more packaging space can be saved.

FIG. 4 shows a state of the safety needle assembly after liquid medicine is drawn and then transported, namely, a state in which the liquid medicine, after being drawn by the safety needle assembly, is transported from place to place. At this time, the needle tube 11 is covered by the protection arm 6, but only located at an opening of the protection arm, i.e., the protection arm 6 is located at a temporary protection position (the fourth middle position). It can be seen that the temporary protection position is located between the full protection position and the packaged position.

Referring to FIGS. 6-9, the protection arm 6 is an arm-like structural member having a generally "U"-shaped cross section and extending along a longitudinal axis, and comprises a bottom protection wall 63 and a pair of side protection walls 61 extending from opposite sides of the bottom protection wall 63. In the present application, a side of the protection arm 6 which is adjacent to the needle hub in use is called a "proximal side", whereas a side away from the needle hub is called a "distal side". The bottom protection wall 63, the pair of side protection walls 61, and a first end wall 62 (proximal end potion) and a second end wall 64 respectively located at the proximal side and the distal side form an opening 60 of the protection arm 6.

For convenience of description, in the present application, a direction in which the protection arm 6 moves towards the full protection position shown in FIG. 5 relative to the connecting portion 2 (or the needle hub 12) is called a "first direction" of the protection arm, and a direction in which the protection arm 6 rotates towards the second in-use position shown in FIG. 3 is called a "second direction" of the protection arm.

Figure 8:
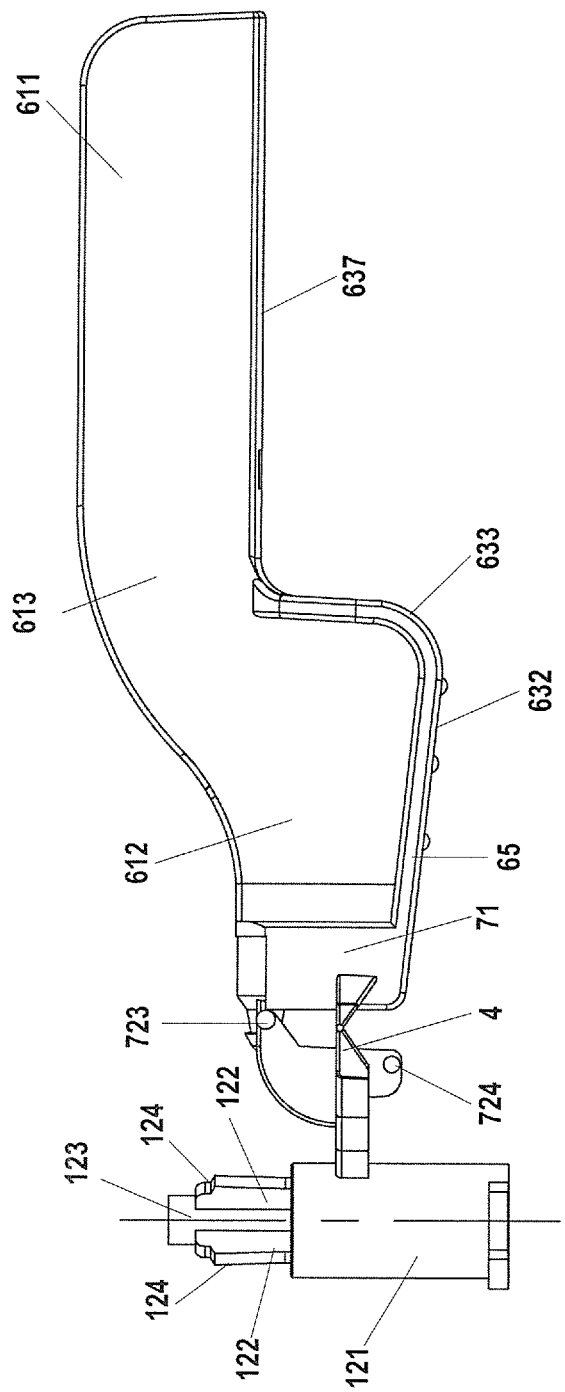
FIG. 8 is a side view of the needle hub and the needle protection device of FIG. 1.
Figure 9:
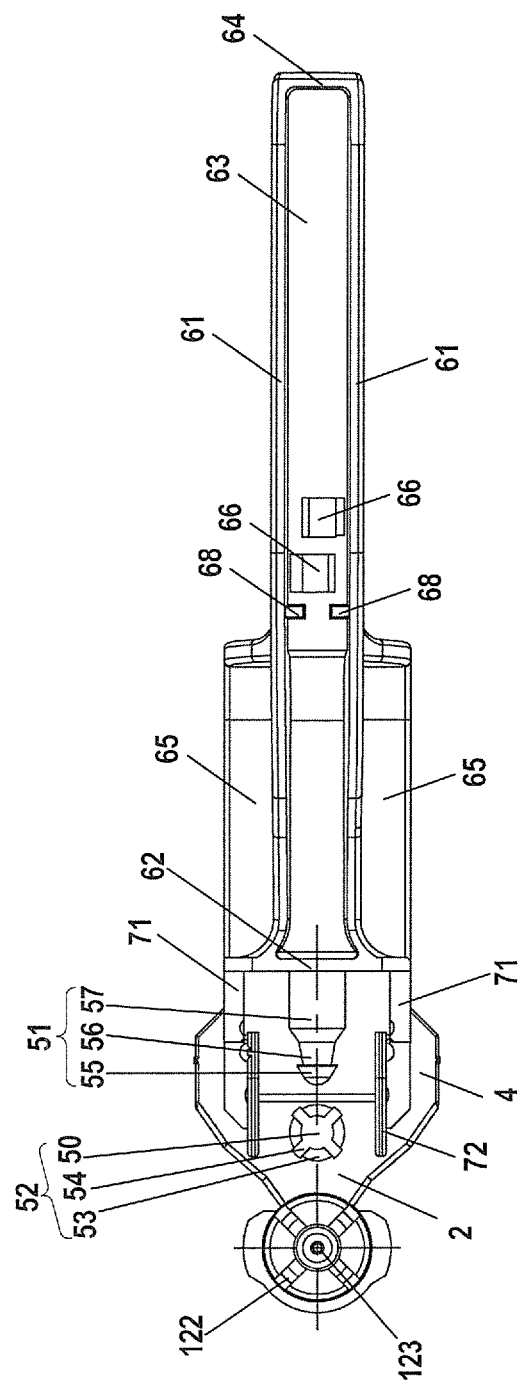
FIG. 9 is a top view of the needle hub and the needle protection device of FIG. 1.
Figure 10:
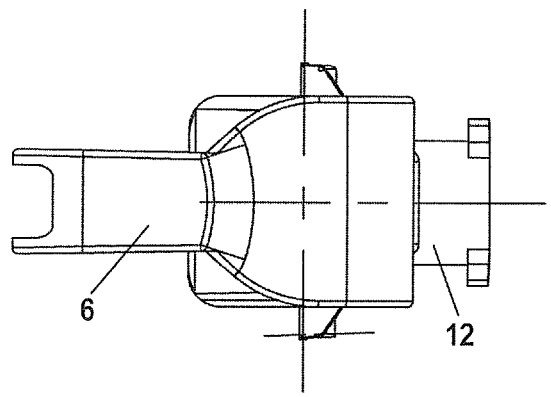
FIG. 10 is a right view of the needle hub and the needle protection device of FIG. 9.
Figure 11:
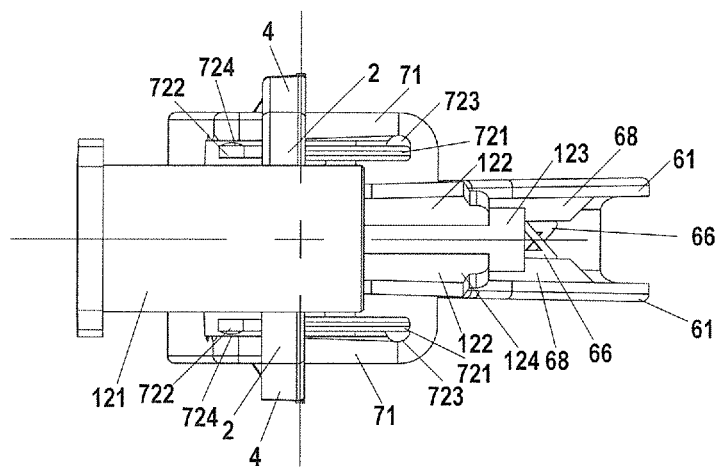
FIG. 11 is a left view of the needle hub and the needle protection device of FIG. 9.
Figure 12:
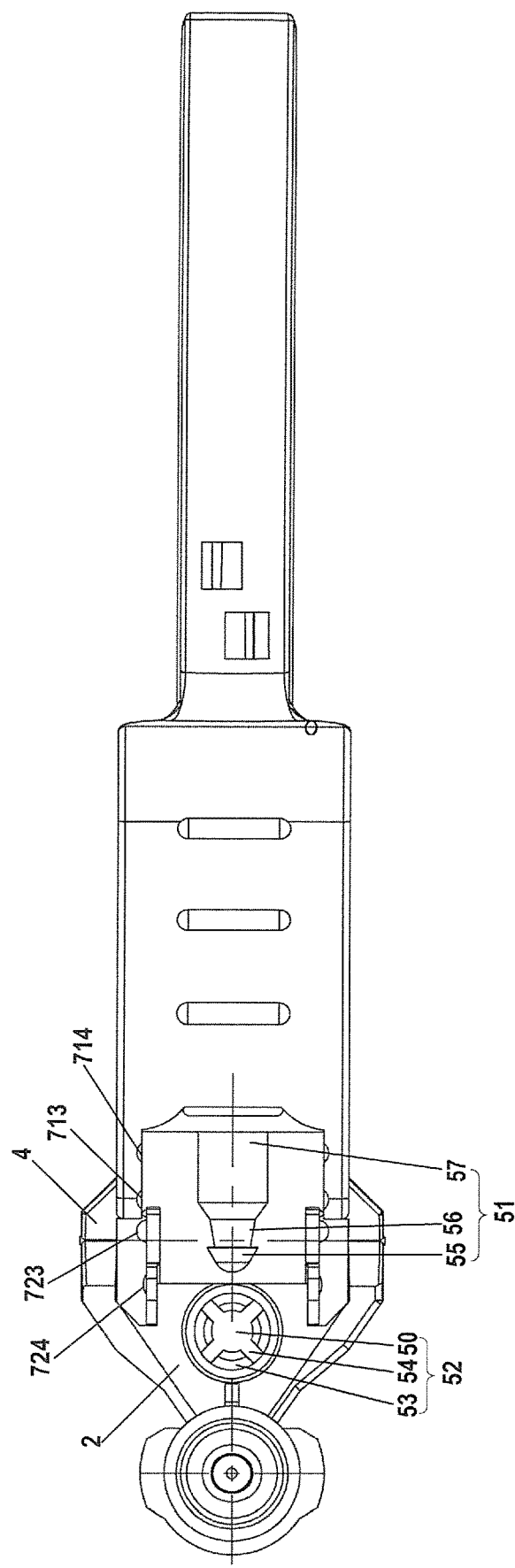
FIG. 12 is a bottom view of the needle hub and the needle protection device of FIG. 9, with a part thereof cut away.

As most clearly shown in FIG. 8, the side protection wall 61 of the protection arm 6 comprises a first side protection wall 611 at the distal side, a second side protection wall 612 at the proximal side and a third side protection wall 613 between the first and second side protection walls. The first side protection wall 611 protrudes more towards the first direction relative to the second side protection wall 612, or the first side protection wall 611 is positioned beyond the second side protection wall 612 in the first direction. The third side protection wall 613 transits from the second side protection wall 612 to the first side protection wall 611 along the first direction. This transition is preferably a smooth transition as shown in FIG. 8. However, this transition may not necessarily be smooth.

The bottom protection wall 63 of the protection arm 6 comprises a first bottom protection wall 631 at the distal side, a second bottom protection wall 632 at the proximal side, and a third bottom protection wall 633 between the first and second bottom protection walls. The first bottom protection wall 631 protrudes more towards the first direction relative to the second bottom protection wall 632, or the first bottom protection wall 631 is positioned beyond the second bottom protection wall 632 in the first direction. The third bottom protection wall 633 transits from the second bottom protection wall 632 to the first bottom protection wall 631 along the first direction.

The first side protection wall 611 and the first bottom protection wall 631 are positioned beyond the second side protection wall 612 and the second bottom protection wall 632 in the first direction so that between a proximal portion of the protection arm 6 and the needle hub is provided a space enough to form a holding member and a positioning arm (to be described in detail in the following text).

It should be appreciated that the above division of the side protection wall and the bottom protection wall are only for depiction purpose and does not mean that parts of the side protection wall and the bottom protection wall are physically separated from one another.

In the example shown in FIG. 8, the third bottom protection wall 633 forms a stepped portion between the first and second bottom protection walls 631, 632. Such third bottom protection wall 633 in a step form provides a surface on which a finger applies a force to push the protection arm 6.

As shown in FIGS. 6-9, a flange 65 is formed on each of both external sides of the second bottom protection wall 632 and the third bottom protection wall 633. In an embodiment, the flange 65 may be integrally formed with the second bottom protection wall 632 and the third bottom protection wall 633. The flange 65 can be used to safely push and press the protection arm 6 from the position shown in FIG. 1 or 4 to the position shown in FIG. 2 or 3, for example, as a gripper from the packaged position to the in-use position upon drawing the liquid medicine. Besides, the flange 65 further increases the area of the third bottom protection wall 633 as a force-applying surface. The first end wall 62 can extend to both sides to flush with the edge of the flange 65.

On a surface of the second bottom protection wall 632 facing in the second direction may further be formed with a structure for increasing friction, such as anti-slip ribs 634 as shown.

In a preferred embodiment, edge portions of respective walls and joints of adjacent walls may be all chamfered or filleted.

As shown in FIG. 5, when the protection arm 6 rotates to the full protection position, the needle tube 11 of the needle 10 passes through the opening 60 of the protection arm 6 into the protection arm 6. In order to further prevent the needle tube 11 from being separated from the protection arm 6, referring to FIGS. 5, 6, 9 and 11, the protection arm 6 may further comprise a hook-shaped member 66 extending a predetermined distance from the first bottom protection wall 631 in the first direction and then bending towards the first bottom protection wall 631. By virtue of this hook-shaped member 66, the needle tube 11 can be easily guided into a space between the hook-shaped member 66 and the first bottom protection wall 631 and "hooked" by the hooked-shaped member 66 and thereby maintained in this space in an unretreatable manner.

In a further preferred embodiment, the protection arm 6 may comprise two or more hook-shaped members 66 (two are shown in the figures). These hook-shaped members 66 are arranged in a longitudinal direction of the protection arm 6 so that their "hooks" are staggeredly opposite to one another. This staggeredly opposite arrangement facilitates more accurate guidance of the needle tube 11.

In a more preferred embodiment, referring to FIGS. 5, 6, 9 and 11, a pair of guide ribs 68 having a guide ramp at a top end thereof may be provided along the inside of the two first side protection walls 611 to restrain the needle tube 11 to the position of the hook-shaped member 66. This embodiment is particularly suitable for a situation in which the needle tube 11 deforms after use.

Referring to FIGS. 6, 7, 9 and 12, a first holding member 51 extending to the proximal side is formed on a proximally facing surface of the proximal end portion 62. In the embodiment as shown in the figures, the first holding member 51 is substantially column-like and on the longitudinal axis of the protection arm 6, and comprises a first column-like portion 57 on the proximal end portion 62, a second column-like portion 56 extending from the first column-like portion 57 towards the proximal side and having a reduced radial dimension (e.g., diameter), and a tapered anchor 55 formed at the proximal side of the second column-like portion 56 and having a tip end (front end) facing towards the proximal side. A base of the anchor 55 is larger than that of the second column-like portion 56. Therefore, the second column-like portion 56 is in fact a necked portion between the anchor 55 and the first column-like portion 57. According to another embodiment (not shown), the second column-like portion 56 may not be provided, and the radial dimension of the base of the anchor 55 is made larger than that of the first column-like portion 57.

A through hole 50 may be formed at a substantially central position of the connecting portion 2. Paws 53 are formed on an edge of the through hole 50. The paws 53 extend towards a center of the through hole 50 while are inclined towards a side (the lower side of FIG. 8) opposite the side in which the first holding member 51 lies. The paws 53 may comprise a plurality of paws separated by a plurality of gaps 54. Alternatively, only one paw may be provided and occupy a portion of a circumference of the through hole 50. Alternatively, the paws 53 are disposed around the circumference of the through hole without any gaps. Theoretically, when the paws are disposed along the circumference of the through hole 50, so long as at least one paw is disposed at the side adjacent to the needle hub 12, the object of the present invention can be achieved. An inner circumference (distal end) of the paws 53 or distal ends of the paws 53 and the edge of the through hole 50 define a bore allowing for passage of the end 55. A radial dimension of the bore corresponds to the radial dimension of the second column-like portion 56 of the first holding member 51, or to the radial dimension of the first column-like portion 57 when no second column-like portion 56 is provided. A maximum radial dimension of the bore is smaller than a maximum radial dimension of a base of the anchor 55. The paws 53 are elastic and can elastically deform under a pressure of the anchor 55 of the first holding member 51; after the anchor 55 passes, the paws 53 elastically return and catches the base of the anchor 55, thereby preventing the anchor 55 from retreating reversely. The paws 53 formed around the through hole 50 constitute a second holding member 52 for holding the first holding member 51 in an unretreatable manner to retain the protection arm 6 at the full protection position permanently and prevent the used safety needle assembly from being used again.

Alternatively, the second holding member may be a boss having an inner bore and formed above the connecting portion (i.e., the upper side of FIG. 8, or on the side in which the first holding member of the connecting portion is located), and paws are inclined inward the inner bore around the edge of the inner bore. The anchor of the first holding member can be inserted into the inner bore and held by the paws.

According to another embodiment, the first holding member 51 and the second holding member 52 may be interchanged in position, that is, the first holding member 51 is formed on the connecting portion 2, whereas the second holding member 52 is formed on the proximal end portion.

In the present invention, the anchor may be in any suitable shapes and is not limited to tapered (e.g. conical and pyramid) and hooked shape. So long as the front end of the anchor can pass through the through hole (not limited to a round through hole) defined by the edges (distal ends) of the paws, and the maximum radial dimension of the base of the anchor is larger than the maximum radial dimension of the through hole, an unretreatable engagement of the anchor and the paws can be achieved. In the present invention, the two column-like portion may be, but not limited to a cylinder or a pyramid so long as the maximum radial dimension of the second column-like portion is smaller than the maximum radial dimension of the base of the anchor.

In order to retain the protection arm 6 to the packaged position, the temporary protection position and in-use position as shown in FIGS. 1-4 as stably as possible, the needle protection device according to the present invention may further comprise a pair of positioning arms. In the embodiment as shown, two pairs of positioning arms are symmetrically located on both sides of the first and second holding members.

The packaged position, the temporary protection position and the in-use position are middle positions different from the full protection position. When the protection arm 6 rotates to these middle positions, the two holding members do not engage each other in the unretreatable manner, that is, the two holding members are separatable. This aspect may be implemented by relative positions of the holding members as conventionally designed and relative positions of snap-fitting features mentioned hereunder, and will not be introduced in detail herein in the present invention.

Referring to FIGS. 1-4 and FIGS. 6-9, 11 and 12, according to a preferred embodiment of the present invention, each pair of positioning arms comprise a first positioning arm 71 and a second positioning arm 72. The first positioning arms 71 extend towards the proximal side from both ends of the proximal end portion 62, and their outer surfaces may flush with outer edges of the flanges 65. The second positioning arms 72 are correspondingly formed at opposite sides of the connecting portion 2, and each comprise an upwardly extending upper second positioning arm 721 and a downwardly extending lower second positioning arm 722. As shown in FIG. 8, a direction pointed towards upper side of the figure (the side in which the first connecting member 51 is located) is "upper", and a direction pointed towards lower side of the figure is "lower".

A plurality of pairs of separable snap-fitting features are formed between the first positioning arm 71 and the second positioning arm 72. Each pair of snap-fitting features correspond to a desired retained position of the protection arm 6 upon snap-fitting, said position includes but is not limited to any position shown in FIGS. 1-4. Furthermore, by applying an appropriate force on the protection arm 6 in a rotating direction, each pair of snap-fitting feature can be separated (i.e., they are snap-fitted or engaged in a separable manner) so that the protection arm 6 may be rotated to different positions relative to the connecting portion 2. Different pairs of snap-fitting features may be different to generate different resistance against rotation of the protection arm 6. For example, at the packaged position as shown in FIG. 1, it is usually desired that the protection arm 6 can be prevented from accidental rotation due to vibration during transport. Therefore, a pair of snap-fitting features corresponding to the packaged position may be configured to generate a greater resistance upon snap-fitting. At the temporary protection position as shown in FIG. 4, the safety needle assembly is usually sent from one room to a nearby room of a hospital or clinic without a great vibration, so a pair of snap-fitting features corresponding to the temporary protection position may be configured to generate a smaller resistance upon snap-fitting.

In a specific embodiment as shown in the figures, the upper second positioning arm 721 has an end portion extending towards the first positioning arm 71, and a first protrusion 723 is formed at the end portion. A second protrusion 724 is formed at a lower edge of the lower second positioning arm 722. Three concaves 711, 712 and 713 are formed on a surface of the first positioning arm 71. The first concave 711, the second concave 712 and a groove 714 to be mentioned hereunder are located on a movement trajectory or path of the first protrusion 723 on the positioning arm 71 relative to the positioning arm 71; the third concave 713 is located on a movement trajectory of the second protrusion 724 on the positioning arm 71 relative to the positioning arm 71.

The first concave 711 is located at a proximal top end of the positioning arm 71, and opens at an edge of an upper surface to facilitate entry of the first protrusion 723 into the first concave 711. However, the first concave 711 may not necessarily open on the upper surface. The first concave 711 and the first protrusion 723 constitute a first pair of snap-fitting features, and when they are snap-fitted, the protection arm 6 is positioned at the first in-use position as shown in FIG. 2.

Relative to the first concave 711, the second concave 712 is formed downstream a movement trajectory of the first protrusion 723 relative to the positioning arm 71, i.e., formed at a downward distal position. The second concave 712 and the first protrusion 723 constitute a second pair of snap-fitting features, and when they are snap-fitted together, the protection arm 6 is positioned at the packaged position as shown in FIG. 1.

According to a preferred embodiment of the present invention, a groove 714 is formed downstream of the second concave 713 on the positioning arm 71. A beginning end of the groove 714 (an end adjacent to the second concave 712) can be a fourth concave (not shown). The first protrusion 723 and the fourth concave at the beginning end of the groove 714 constitute a fourth pair of snap-fitting features, and when they are snap-fitted together, the protection arm 6 is positioned at the temporary protection position shown in FIG. 4. As above discussed, the fourth concave may be shallower than other concaves.

After the safety needle assembly is used, and when the protection arm 6 is rotated to the full protection position as shown in FIG. 5, the first protrusion 723 may be configured to slide in the groove 714 so as to reduce a force needed to rotate the protection arm 6. The sliding engagement of the first protrusion 723 and the groove 714 may also guide the movement of the protection arm 6, and facilitates accurate engagement of the first holding member 51 and the second holding member 52.

The third concave 713 may be formed at a proximal lower end of the positioning arm 71, and opens at an edge of a lower surface as shown in the figure. However, the third concave 713 may not necessarily open on the lower surface. The third concave 713 and the second protrusion 723 constitute a third pair of snap-fitting features, and when they are snap-fitted together, the protection arm 6 is positioned at the second in-use position as shown in FIG. 3.

As a preferred embodiment, snap-fitting between respective pairs of snap-fitting features is an elastic snap-fitting, which may be implemented by cantilever structure of the two positioning arms 71 and 72, alternatively or additionally by use of elastic material to manufacture the positioning arms. Alternatively, only one of the two positioning arms 71 and 72 may be elastic. When the protrusion is not located in the concave, elastic deformation will occur between the two positioning arms 71 and 72 due to mutual pressure because of existence of protrusions; when the protrusion moves to the position of the concave, the two positioning arms return their original shapes due to elasticity, and press the protrusion into the concave, thereby positioning the protection arm 6 at a desired position. When a force is applied to the protection arm 6 in a movement direction of the protection arm 6, if the force is sufficient to overcome a resistance caused by elastic deformation of the positioning arms, the protrusion will be separated from the concave. Then, the protection arm 6 begins to rotate until a next position.

Alternatively, the first protrusion 723 may be replaced by an concave, and the first and second concaves 711 and 712 may be replaced by protrusions accordingly; or the second protrusion 724 may be replaced by an concave, and the third concave 713 may be replaced by a protrusion accordingly.

The protrusion and concave may be semi-spherical or crown-shaped, or other shapes.

Referring to FIGS. 6-12, the first positioning arm 71 extending from the proximal end portion of the protection arm 6 is attached to the connecting portion 2 via the hinge member 4. In other embodiment, the hinge member may be used as part of the first positioning arm.

The hinge member 4 and the second positioning arm 72 may be respectively located at inner and outer sides of the first positioning arm 71. For example, in the embodiment as shown in the figures, the second positioning arm 72 is located at the inner side of the first positioning arm 71, and the hinge member 4 is fixedly attached to an outer side surface of the first positioning arm 71.

Figure 20:
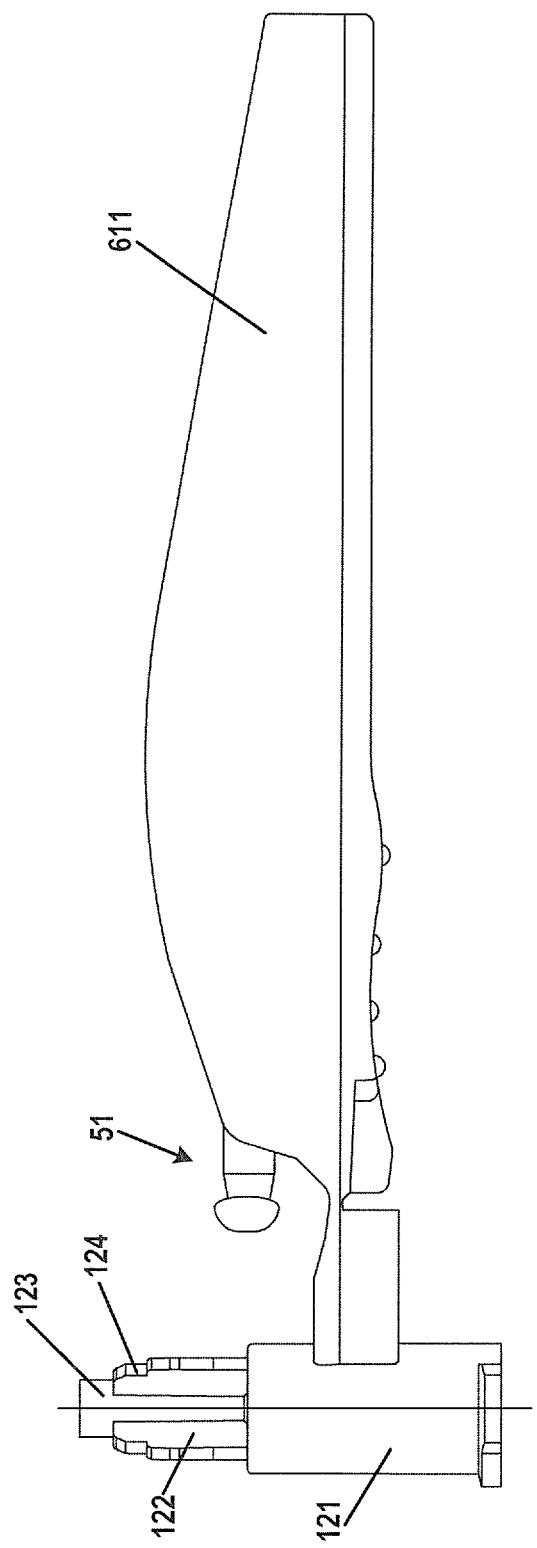
FIG. 20 is a schematic view of the needle protection device without positioning arms.

The positioning arms can be embodied as any other form of positive fit. Alternatively, the positioning arms can be held at any position relative to the protection arm 6 by for example friction force resulted by the tight fit therebetween. Certainly, the positioning arms can be even removed as shown in FIG. 20.

The needle protection device according to the present invention may be a plane-symmetrical structure which is substantially symmetrical relative to a plane (symmetrical plane) in which the longitudinal axis of the protection arm lies (for example, the hook-shaped members 66 and ribs 124 may not be symmetrically distributed relative to the symmetrical plane), wherein the first and second holding members 51 and 52 are located on the symmetrical plane, and respective protection walls and positioning arms are symmetrically distributed relative to the symmetrical plane. In the present invention, the term "inner" means a direction pointing at the symmetrical plane or approaching the symmetrical plane, and "outer" means a direction away from the symmetrical plane or remote from the symmetrical plane.

The protection arm structure of the present invention does not need to use a mold with a slide upon injection molding, thereby simplifying the structure of the mold, substantially improving the number of mold cavities (e.g., up to 96 cavities), greatly facilitating use of a large mold to mass produce molded products by one injection molding, and remarkably reducing the production costs of the protection arm. Furthermore, there are low mold-opening requirements for the protection arm structure of the present invention, which facilitates simplification of the mold structure and reduction of manufacturing and use costs of the mold.

FIGS. 16-19 show a needle protection device according to another embodiment of the present invention. The needle protection device is similar to the above-mentioned needle protection device. Therefore, the same reference numerals are used to denote the same portions or members. The difference between the needle protection device and the above-mentioned needle protection device is that the first holding member 51 with the tapered anchor 55 and the second holding member 52 formed by the paws 53 may be replaced by a hook-like member. In such a case, the through hole 50 may be omitted. According to the teaching of the present invention, those skilled in the art can contemplate that the hook-like holding members may also be replaced by other members known by those skilled in the art which can be engaged in an unretreatable manner.

In the embodiment as shown in FIGS. 16-19, a pair of holding members comprise a first holding member 81 and a second holding member 82. A hook-like portion 85 is formed at a free end 86 of the first holding member 81; the second holding member 82 is a plate-like hook, i.e., a cross-sectional shape of the plate material is hook-like (as can be best seen in FIG. 19). The hook-like portion 85 of the first holding member 81 and the second holding member 82 are configured such that they can be engaged in an unretreatable manner when the protection arm 6 rotates to the full protection position shown in FIG. 5.

In the preferred embodiment as shown in the figures, the first holding member is also plate-shaped and formed on the proximal end portion 62 of the protection arm 6, and has two opposite widthwise surfaces 84 and two opposite thickness surfaces 83. The hook-like portion 85 is formed on each of the two thickness surfaces 83 at the free end 86 of the first holding member 81.

Referring to FIG. 16, two pairs of positioning arms are symmetrically located on both sides of the first holding member 81. The positioning arm 72 of each pair of positioning arms formed on the connecting portion 2 is each formed with a second holding member 82. When the protection arm 6 rotates to the full protection position, the two hook-like portions 85 of the first holding member 81 and the two second holding members 82 are respectively engaged in an unretreatable manner.

Figure 17:
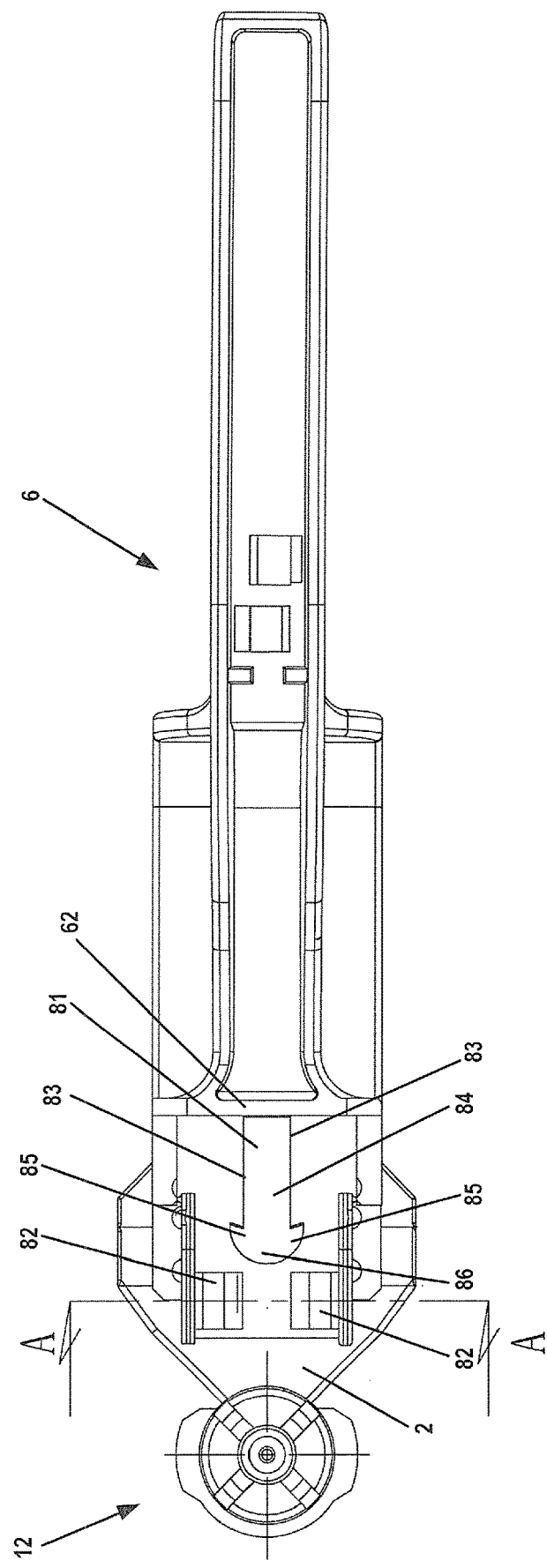
FIG. 17 is a top view of the needle protection device as shown in FIG. 16.
Figure 18:
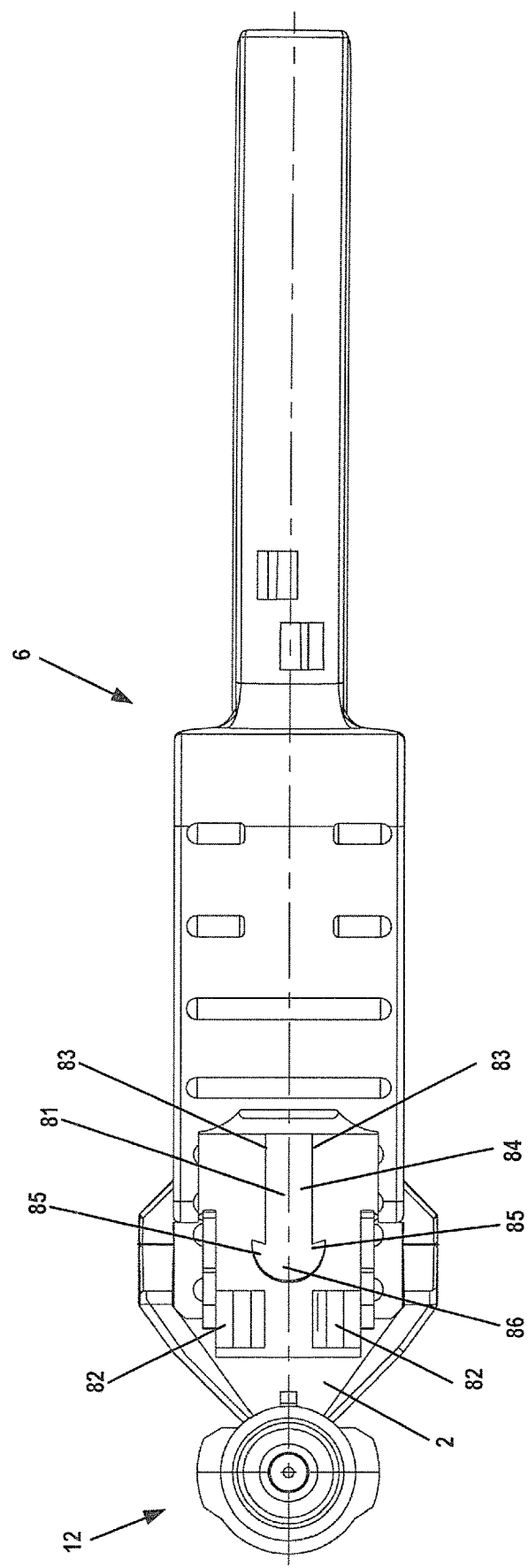
FIG. 18 is a bottom view of the needle protection device as shown in FIG. 16.

As shown in FIGS. 16-18, the free end 86 of the first holding member 82 forms a substantially tapered shape, i.e., a widthwise dimension thereof gradually increases from the tip of the free end 86 to the hook-like portions 85. The transition from the free end to the hook-like portions may be a rectilinear transition, an arcuate transition or other curved transitions, preferably a smooth transition.

Figure 19:
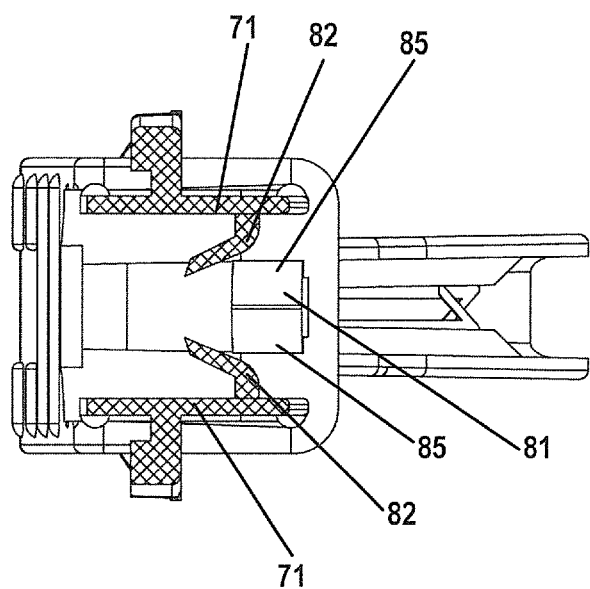
FIG. 19 is a cross-sectional view taken along the line A-A of FIG. 17

Referring to FIG. 19, the hook-like second holding member 82 has a cross section of an arm extending curvedly downwardly. This structure itself enables the second holding member 82 to have an elastically deforming capability. When the free end 86 with a substantially tapered surface shown in FIGS. 16-18 contacts with the second holding members 82, the free end can easily enable the second holding members 82 to deform elastically and pass over the second holding members 82. When the free end 86 passes over the second holding members 82, the second holding members 82 elastically return. At this time, if the first holding member 81 intends to retreat, the second holding members 82 will be snap-fitted with the hook-like portions 85 of the first holding member 81, thereby preventing the retreat of the first holding member 81. That is, the hook-like portions of the first holding member 81 are engaged with the second holding members 82 in an unretreatable manner.

In a further preferred embodiment (not shown), a hook-like portion is additionally formed on one widthwise surface 84 of the free end 86 of the first holding member 81 and configured the same as the above-mentioned hook-like portions 85. Correspondingly, a second holding member the same as the above-mentioned holding members 82 may be formed on the connecting portion. When the protection arm 6 rotates to the full protection position, the three hook-like portions 85 of the first holding member 81 are respectively engaged with three second holding members 82 in an unretreatable manner.

In a still further preferred embodiment (not shown), no second holding members may be provided on the positioning arms. The above-mentioned second holding member 82 may be only formed on the connecting portion 2. In such a case, the first holding member 81 may be only formed with one hook-like portion 85 corresponding to the second holding member 82 so that when the protection arm 6 rotates to the full protection position, the hook-like portion 85 of the first holding member 81 is engaged with the second holding member 82 in an unretreatable manner.

Although the present invention has been particularly described with reference to the accompany drawings in the above, it should be understood by those skilled in the art that the above particular descriptions are only exemplary and for illustrative purpose, but not to limit the protective scope of the present invention which is only defined by the appended claims. In light of the teaching of the present invention, those skilled in the art may make various modifications, changes or substitutions under particular circumstances which fall within the protective scope of the present invention.

What is claimed is:

1. A needle protection device comprising:
a connecting portion configured to engage with a needle hub of a needle;
a protection arm configured to receive a needle tube of the needle therein and having a proximal end portion adjacent to the connecting portion;
a hinge member connected between the connecting portion and the protection arm so that the protection arm is rotatable relative to the connecting portion; and
a pair of holding members formed on the proximal end portion of the protection arm and the connecting portion respectively, wherein the pair of holding members are configured to be engaged with each other in an unretreatable manner when the protection arm rotates to a full protection position in which the protection arm is most proximate to the needle tube of the needle relative to the connecting portion;
wherein the pair of holding members comprises:
a first holding member comprising a first column-like portion and a tapered anchor formed on the first column-like portion; and
a second holding member comprising a through hole and a plurality of elastic paws formed on an edge of the through hole, wherein the plurality of elastic paws extend toward a center of the through hole,
wherein a bore is defined by either distal ends of the plurality of elastic paws, or by the distal ends of the plurality of elastic paws in combination with the edge of the through hole,
wherein the bore has a maximum radial dimension of the bore that is smaller than a maximum radial dimension of a base of the tapered anchor, and
wherein the plurality of elastic paws are configured such that the distal ends of the plurality of elastic paws can recover elasticity after a front end of the tapered anchor passes through the bore and catches the base of the tapered anchor in the unretreatable manner when the protection arm rotates to the full protection position.

2. The needle protection device according to claim 1, wherein the device further comprises a pair of positioning arms formed on the proximal end portion of the protection arm and the connecting portion respectively, and being formed with at least one pair of complementary snap-fitting features, the at least one pair of snap-fitting features being configured to be engaged with each other in a separable manner when the protection arm rotates to at least one middle position other than the full protection position relative to the connecting portion, and
wherein the at least one middle position is remote from the needle tube of the needle relative to the full protection position so that at the at least one middle position, the pair of holding members are located in a non-engaged position.

3. The needle protection device of claim 2,
wherein the pair of positioning arms comprises a first positioning arm and a second positioning arm, and
wherein:
a first protrusion is formed on an end portion of the second positioning arm extending towards the first positioning arm,
at least one concave surface comprises a first concave surface which is formed on the first positioning arm, wherein the first concave surface is configured to move relative to the first protrusion, and
the first protrusion is configured to be engaged with the first concave surface in a separable manner to position the protection arm at a first middle position, the first protrusion and the first concave surface constituting a first pair of snap-fitting features.

4. The needle protection device of claim 3, wherein:
the at least one concave surface further comprises a second concave surface, which is formed on the first positioning arm, wherein the first concave surface is configured to move relative to the first protrusion, and
the first protrusion is configured to be engaged with the second concave surface in a separable manner to position the protection arm at a second middle position, the first protrusion and the second concave surface constituting a second pair of snap-fitting features.

5. The needle protection device of claim 4,
wherein the second positioning arm comprises an upper second positioning arm and a lower second positioning arm,
wherein the first protrusion is formed on an end portion of the upper second positioning arm extending towards the first positioning arm,
wherein the first protrusion is configured to be engaged with the first concave surface and the second concave surface in turn when the protection arm rotates in the direction of the full protection position relative to the connecting portion,
wherein a second protrusion is formed at a lower edge of the lower second positioning arm,
wherein a third concave surface is formed on the first positioning arm, wherein the first concave surface is configured to move relative to the second protrusion, and
wherein the second protrusion is configured to be engaged with the third concave surface in a separable manner to position the protection arm at a third middle position, the second protrusion and the third concave surface constituting a third pair of snap-fitting features.

6. The needle protection device of claim 2, wherein the needle protection device comprises two pairs of positioning arms which are symmetrically located on both sides of the pair of holding members.

7. The needle protection device according to claim 1,
wherein the first holding member is formed on the proximal end portion of the protection arm, and the second holding member is formed on the connecting portion, and
wherein the plurality of elastic paws are formed on the edge of the through hole, extend towards the center of the through hole and are inclined towards a side opposite a side in which the first holding member lies, so that when the protection arm rotates to the full protection position, the front end of the tapered anchor is allowed to pass through the bore and beyond the plurality of elastic paws, and the base of the tapered anchor thereof is caught by the plurality of elastic paws in the unretreatable manner.

8. The needle protection device according to claim 1,
wherein the first holding member is formed on the connecting portion, and the second holding member is formed on the proximal end portion of the protection arm, and
wherein the plurality of elastic paws, which are formed on the edge of the through hole, extend towards the center of the through hole and are inclined towards a side opposite a side in which the first holding member lies, so that when the protection arm rotates to the full protection position, the front end of the tapered anchor is allowed to pass through the bore and beyond the plurality of elastic paws, and the base thereof is caught by the plurality of elastic paws in the unretreatable manner.

9. The needle protection device according to claim 1,
wherein the first holding member further comprises a second column-like portion between the tapered anchor and the first column-like portion,
wherein the second column-like portion has a radial dimension smaller than that of the first column-like portion, and
wherein a radial dimension of the base of the tapered anchor is larger than that of the second column-like portion.

* * * * *